United States Patent
Limon et al.

(10) Patent No.: US 7,666,342 B2
(45) Date of Patent: Feb. 23, 2010

(54) METHOD OF MANUFACTURING A STENT FROM A POLYMER TUBE

(75) Inventors: Timothy A. Limon, Cupertino, CA (US); Daniel A. Castro, Santa Clara, CA (US); David C. Gale, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 160 days.

(21) Appl. No.: 11/771,967

(22) Filed: Jun. 29, 2007

(65) Prior Publication Data

US 2009/0001633 A1    Jan. 1, 2009

(51) Int. Cl.
B29C 35/06    (2006.01)

(52) U.S. Cl. .................. 264/535; 264/573; 264/404; 264/402

(58) Field of Classification Search .......... 264/535, 264/573; 425/526
See application file for complete search history.

(56) References Cited

U.S. PATENT DOCUMENTS

| | | |
|---|---|---|
| 3,636,956 A | 1/1972 | Schneider |
| 4,547,416 A | 10/1985 | Reed et al. |
| 4,698,196 A | 10/1987 | Fabian |
| 4,702,884 A | 10/1987 | Goldstein |
| 4,957,687 A | 9/1990 | Akman et al. |
| 4,987,025 A | 1/1991 | Shiraki et al. |
| 5,087,394 A | 2/1992 | Keith |
| 5,108,416 A | 4/1992 | Ryan et al. |
| 5,116,365 A | 5/1992 | Hillstead |
| 5,147,302 A | 9/1992 | Euteneuer et al. |
| 5,500,013 A | 3/1996 | Buscemi et al. |

(Continued)

FOREIGN PATENT DOCUMENTS

EP    0 583 170    2/1994

(Continued)

OTHER PUBLICATIONS

Answers.com blow molding; retrieved from www.answer.com/blow%20molding#Stretch_blow_molding, Jun. 26, 2009, 11 pgs.

(Continued)

*Primary Examiner*—Christina Johnson
*Assistant Examiner*—Roshanak Aryan-Nejad
(74) *Attorney, Agent, or Firm*—Squire, Sanders & Dempsey, L.L.P.

(57) ABSTRACT

A blow molding apparatus for expanding a polymer tube and a method for fabricating a stent using the apparatus is disclosed. The polymer tube is disposed within a tubular mold, over which a heated ring is made of a material having thermal conductivity greater than the tubular mold is translated. The ring is heated with heated fluid streams applied directly onto an outer surface of the ring, or heated fluid circulated within the ring, or an electrically resistive coil within the ring, or combinations thereof. The heated ring uniformly heats a circumference of the tubular mold that, in turn, uniformly heats a circumferential band of the polymer tube. The heated polymer tube is progressively expanded radially and axially while the ring is translated longitudinally over the polymer tube. The expanded polymer tube can be heat set and cooled prior to removal from the tubular mold.

28 Claims, 9 Drawing Sheets

U.S. PATENT DOCUMENTS

| | | | |
|---|---|---|---|
| 5,628,786 A | | 5/1997 | Banas et al. |
| 5,670,161 A | | 9/1997 | Healy et al. |
| 5,891,386 A | | 4/1999 | Deitermann et al. |
| 6,572,813 B1 * | | 6/2003 | Zhang et al. ............... 264/519 |
| 6,626,939 B1 | | 9/2003 | Burnside et al. |
| 6,645,422 B2 | | 11/2003 | Jung et al. |
| 7,066,952 B2 | | 6/2006 | Igaki |
| 7,070,615 B1 | | 7/2006 | Igaki |
| 7,083,639 B2 | | 8/2006 | Guinan et al. |
| 7,128,868 B2 | | 10/2006 | Eidenschink |
| 2001/0014821 A1 * | | 8/2001 | Juman et al. ............... 623/1.11 |
| 2002/0077592 A1 | | 6/2002 | Barry |
| 2002/0138133 A1 | | 9/2002 | Lenz et al. |
| 2002/0151965 A1 | | 10/2002 | Roth |
| 2003/0028241 A1 | | 2/2003 | Stinson |
| 2003/0028246 A1 | | 2/2003 | Palmaz et al. |
| 2003/0055488 A1 | | 3/2003 | Igaki |
| 2003/0083732 A1 | | 5/2003 | Stinson |
| 2003/0187158 A1 | | 10/2003 | Preuschen et al. |
| 2003/0208254 A1 | | 11/2003 | Shortt |
| 2003/0226833 A1 | | 12/2003 | Shapovalov et al. |
| 2004/0000361 A1 | | 1/2004 | Trozera |
| 2004/0098090 A1 | | 5/2004 | Williams et al. |
| 2005/0004663 A1 | | 1/2005 | Llanos et al. |
| 2005/0137678 A1 | | 6/2005 | Varma |
| 2005/0177130 A1 * | | 8/2005 | Konstantino et al. ........ 604/509 |
| 2005/0187615 A1 | | 8/2005 | Williams et al. |
| 2005/0196485 A1 | | 9/2005 | Cass et al. |
| 2006/0020330 A1 | | 1/2006 | Huang et al. |
| 2006/0076708 A1 | | 4/2006 | Huang et al. |
| 2006/0211952 A1 | | 9/2006 | Kennedy |
| 2006/0224226 A1 | | 10/2006 | Huang et al. |
| 2007/0038290 A1 | | 2/2007 | Huang et al. |
| 2007/0253996 A1 | | 11/2007 | Bin et al. |
| 2007/0253999 A1 | | 11/2007 | Huang et al. |
| 2007/0282433 A1 | | 12/2007 | Limon et al. |
| 2007/0290412 A1 | | 12/2007 | Capek et al. |
| 2007/0293938 A1 | | 12/2007 | Gale et al. |
| 2008/0001333 A1 | | 1/2008 | Kleine et al. |
| 2009/0005860 A1 | | 1/2009 | Gale et al. |
| 2009/0012598 A1 | | 1/2009 | Abbate et al. |
| 2009/0146348 A1 | | 6/2009 | Huang et al. |

FOREIGN PATENT DOCUMENTS

| | | |
|---|---|---|
| GB | 2 102 827 | 2/1983 |
| WO | WO 97/32546 | 9/1997 |
| WO | WO 00/12147 | 3/2000 |
| WO | WO 01/15633 | 3/2001 |
| WO | WO 2004/067262 | 8/2004 |
| WO | WO 2006/014747 | 2/2006 |

OTHER PUBLICATIONS www.engineeringtoolbox.com/thermal/conductivity/d_429.html., Jun. 26, 2009, 4 pgs.

* cited by examiner

METHOD OF MANUFACTURING A STENT FROM A POLYMER TUBE

BACKGROUND OF THE INVENTION

1. Field of the Invention

This invention relates generally to methods of manufacturing a stent and, more particularly, to methods of manufacturing a stent from a polymer tube.

2. Description of the State of the Art

Stents function to hold open and sometimes expand a segment of a blood vessel or other anatomical lumen such as urinary tracts and bile ducts. Stents are often used in the treatment of atherosclerotic stenosis in blood vessels. A "lumen" refers to a cavity of a tubular organ such as a blood vessel.

A stent has a cylindrical shape and includes a pattern with a number of interconnecting structural elements or struts. Some stents are designed so that they may be radially compressed (crimped) and radially expanded (to allow deployment). A stent can be fabricated from a tube that has been laser cut to form a stent pattern.

The stent must be able to satisfy a number of mechanical requirements. First, the stent must withstand structural loads, namely radial compressive forces, imposed on the stent as it supports the walls of a lumen. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity. Once expanded, the stent must adequately maintain its size and shape throughout its service life despite the various forces that may come to bear on it, including cyclic loading, which is induced by a beating heart.

The stent can be manufactured from a polymer tube. To increase the strength and rigidity of the polymer tube, the polymer tube can be expanded radially and/or axially so as to orient the polymer molecules of the tube in a manner that provides greater strength and rigidity along the direction of expansion. The polymer tube can be expanded in a tubular mold in order limit the amount of expansion. Typically, the polymer tube is heated within the tubular mold to allow for the desired expansion. Selected segments of the polymer tube can be heated, which transfers heat to segments of the polymer tube that are to be expanded.

Highly uniform radial expansion of the polymer tube is often desired so that a stent that is eventually formed from the polymer tube will have highly uniform mechanical properties, such as strength and rigidity.

SUMMARY OF THE INVENTION

Briefly and in general terms, the present invention is directed to a method of method of manufacturing a stent from a polymer tube. In aspects of the present invention, the manufacturing method comprises translating a heated ring disposed over a tubular mold with a polymer tube disposed within the tubular mold, wherein the heated ring uniformly heats a circumference of the mold and the polymer tube as the heated ring translates along the tubular mold, and allowing the polymer tube to radially expand as the heated ring translates along the tubular mold.

In other aspects of the invention, the method comprises translating a heated ring disposed over a tubular mold with a polymer tube disposed within the tubular mold, wherein the heated ring is heated by a heated fluid to allow the ring to uniformly heat a circumference of the mold and the polymer tube as the heated ring translates along the tubular mold, moving the heated fluid through an outlet of a nozzle while translating the heated ring, the nozzle outlet in communication with the ring disposed over the tubular mold, and allowing the polymer tube to radially expand as the heated ring translates along the tubular mold.

The method, in yet other aspects of invention, comprises translating a heated ring disposed over a tubular mold with a polymer tube disposed within the tubular mold, wherein the heated ring includes a heating conduit disposed within it to allow the ring to uniformly heat a circumference of the mold and the polymer tube as the heated ring translates along the tubular mold, thermally energizing the heating conduit while translating the heated ring, the nozzle outlet in communication with the ring disposed over the tubular mold, and allowing the polymer tube to radially expand as the heated ring translates along the tubular mold.

The features and advantages of the invention will be more readily understood from the following detailed description which should be read in conjunction with the accompanying drawings.

DETAILED DESCRIPTION OF THE INVENTION

Various embodiments of the present invention may be applied to stents and, more generally, to implantable medical devices such as, but not limited to, self-expandable stents, balloon-expandable stents, stent-grafts, vascular grafts, or generally, tubular implantable medical devices.

A stent can have virtually any structural pattern that is compatible with a bodily lumen in which it is implanted. Typically, a stent is composed of a pattern or network of circumferential and longitudinally extending interconnecting structural elements or struts. In general, the struts are arranged in patterns, which are designed to contact the lumen walls of a vessel and to maintain vascular patency. A myriad of strut patterns are known in the art for achieving particular design goals. A few of the more important design characteristics of stents are radial or hoop strength, expansion ratio or coverage area, and longitudinal flexibility. The present invention is applicable to virtually any stent design and is, therefore, not limited to any particular stent design or pattern. One embodiment of a stent pattern may include cylindrical rings composed of struts. The cylindrical rings may be connected by connecting struts.

In some embodiments, a stent of the present invention may be formed from a tube by laser cutting the pattern of struts in the tube. The stent may also be formed by laser cutting a polymeric sheet, rolling the pattern into the shape of the cylindrical stent, and providing a longitudinal weld to form the stent. Other methods of forming stents are well known and include chemically etching a polymeric sheet and rolling and then welding it to form the stent.

Figure 1:
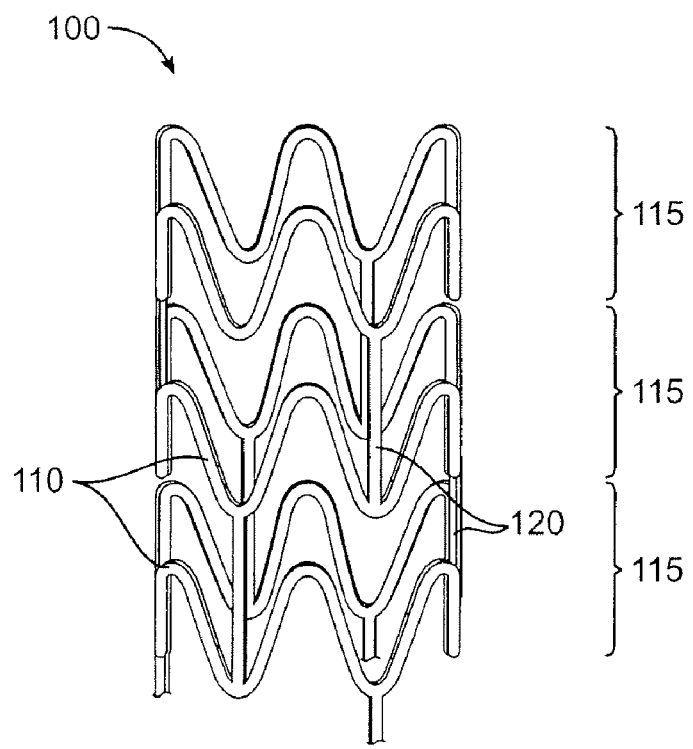
FIG. 1 is a perspective view showing an end-region of a stent.

Referring now in more detail to the exemplary drawings for purposes of illustrating embodiments of the invention, wherein like reference numerals designate corresponding or like elements among the several views, there is shown in FIG. 1 a distal end region of an exemplary stent 100 with struts 110 that form cylindrical rings 115. Three rings 115 are shown connected by a plurality of connecting struts 120. The total number of rings 115 is not limited to what is illustrated, and the stent can have more or less rings as appropriate for the intended use of the stent. The cross-section of the struts 120 is rectangular-shaped. The cross-section of struts is not limited to what has been illustrated, and therefore, other cross-sectional shapes are applicable with embodiments of the present invention. Also, the pattern should not be limited to what has been illustrated as other stent patterns are easily applicable with embodiments of the present invention.

As indicated above, it is important for a stent to have high radial strength so that after it is deployed from a crimped state it can support a lumen. In general, deforming a polymer construct, such as a polymer tube, can strengthen the polymer of the construct along an axis of deformation. In some embodiments of fabricating a stent from a polymer tube, the polymer tube can be radially expanded and the stent can be fabricated from the polymer tube in its expanded state.

Figure 2:
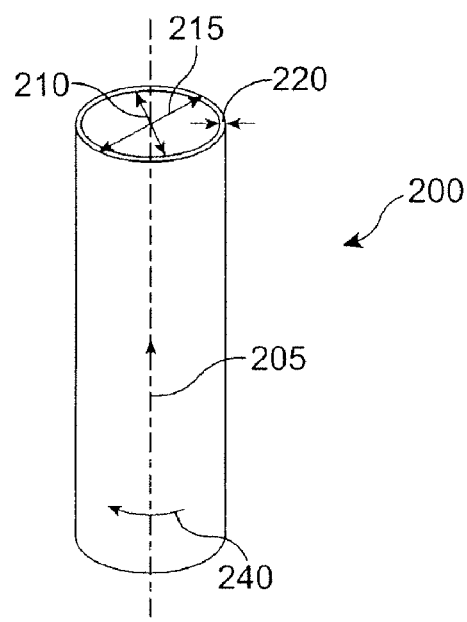
FIG. 2 is a perspective view showing polymer tube for use in fabricating a stent.

FIG. 2 depicts an exemplary polymer tube 200 for use in forming a stent. The polymer tube 200 has a longitudinal axis 205, an inner diameter 210, outer diameter 215 and thickness 220. The polymer tube 200 can be radially deformed by applying stress in the radial direction, which strengthens tube 200 in a circumferential direction 240, thereby increasing the radial strength of the tube. Strength in the axial direction can also be increased by axial deformation. The uniformity of the radial expansion impacts the concentricity of the expanded tube and the uniformity of expanded thickness 220. These properties are important to the mechanical stability of the stent fabricated from the tube 200.

The embodiments disclosed herein relate to fabricating a polymeric stent, such as depicted in FIG. 1, that includes methods for expanding a polymer tube using blow molding. The embodiments of blow molding described herein can increase the uniformity of radial expansion of a tube. As a result, a stent fabricated from the tube has more uniform mechanical properties and greater mechanical stability.

In a blow molding process, a polymer tube is disposed within a mold having an outside diameter that may be a desired expanded diameter of the tube. A radial force is applied to the inside the tube, typically by blowing a gas into the tube within the mold. A heat source is positioned adjacent to the mold and heats a circumference of the mold. The heated circumference of the mold, in turn, heats an adjacent circumference of the tube. Highly uniform expansion of the tube is facilitated by highly uniform heating around the circumference of the tube since portions of the tube that are heated more tend to expand more readily than other portions of the tube.

The uniformity of the heating depends at least in part on the nature of the heat source. Typically, a mold is made from a material having a relatively low thermal conductivity, such as, but not limited to, glass. Glass has the advantage of easily being formed to have a very smooth inner mold surface and, also, the deformed polymer tube does not stick to glass. Thus, due to the low thermal conductivity of the mold, if the heat source consists of heated air streams that are concentrated only on small areas along a circumference of the mold, the small areas will be significantly hotter than other areas around the circumference. As a result, the heat transferred by the mold to the tube may be circumferentially inhomogeneous or nonuniform which can cause localized hot spots on the tube to develop. Such circumferentially nonuniform heating can result in nonuniformity of expansion of the polymer tube and a lowering of concentricity in the expanded polymer tube. A lowering of concentricity is characterized by an increased variation in wall thickness of the expanded polymer tube along its circumference. Low concentricity and high variation in wall thickness is often undesirable since highly uniform dimensions throughout the tube provide mechanical stability to a stent.

Various embodiments of the present invention relate to methods of blow molding polymer tubes that allow more uniform heating around the circumference of a mold resulting in greater uniformity in deformation of the tube and fabricating a stent from the expanded tube. A tube that is more uniformly expanded during blow molding allows fabrication of a stent therefrom that has more uniform mechanical properties Certain embodiments of the present invention include blow molding with a thermally conductive ring slidably disposed over a circumference of the mold. Preferably, the material of the ring is selected to have a greater thermal conductivity than the mold material, such that the rate of heat transfer in the ring is greater than that in the mold. Consequently, when the ring is heated, such as with heated air streams that are concentrated only on small areas of the ring, heat is distributed to other areas of the ring outside the path of the heated air streams, resulting in a circumferential heating of the mold that is more uniform as compared to heating the mold by applying the heated air streams directly to the mold. The uniform circumferential heating of the mold, in turn, prevents or reduces localized hot spots on the mold and on adjacent portions of the polymer tube within the mold.

In some embodiments, the mold can be composed of a material having a relatively low thermal conductivity between 0.1-10 W/m-K. For example, the mold can be glass, which can have a thermal conductivity of 0.88 W/m-K at 150 deg. C., 1.36 W/m-K at 300 deg. C., and 1.50 W/m-K at 400 deg. C. In other embodiments, the mold material can be metal or other material, as appropriate for forming a mold with a smooth surface.

The ring material can have a thermal conductivity that is two, 20, 50, 100, 200, 300, or more than 400 times that of the mold material. In exemplary embodiments, the thermal conductivity of the ring material can be at least 20, 50, 100, 200, 300, or more than 400 W/m-K. In some embodiments, the ring material can be a metal. Exemplary metals include, but are not limited to, aluminum, gold, copper, nickel, steel, stainless steel, oxides of such metals, and alloys and mixtures thereof. Aluminum can have a thermal conductivity of 255 W/m-K at 125 deg. C. and 250 W/m-K at 225 deg. C. Preferably, a metal is selected that resists degradation such as may occur due to oxidation when subjected to high temperatures. The metal may also be treated to resist degradation with use at high temperatures. If the ring is made of aluminum, the ring may be anodized to resist degradation.

In other embodiments, the ring material has the same or lower thermal conductivity than that of the mold material. Uniform heating of the ring and, thus, the mold and the polymer tube within the mold, can be achieved with one or more heating elements or heat sources that are uniformly distributed within or on the ring.

Figure 3:
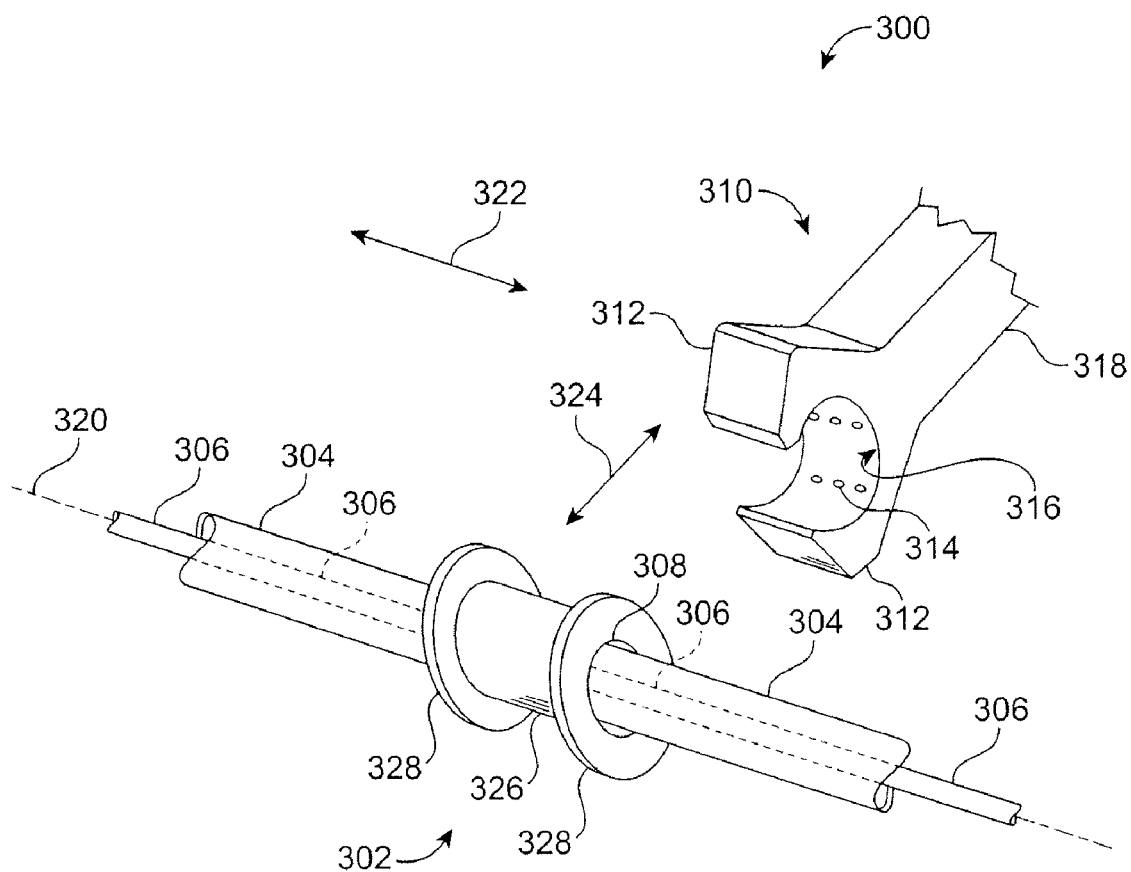
FIG. 3 is a perspective view of a blow molding apparatus showing a tubular mold containing an unexpanded polymer tube and carrying a slidable sleeve-like ring for uniformly heating a segment of the mold, a movable heating nozzle is shown at a distance away from the ring.

FIGS. 3-6 depict an exemplary blow molding apparatus 300 and method of the present invention. In FIG. 3, a ring 302 is disposed over a circumference of a tubular mold 304. An unexpanded polymer tube 306 is disposed within the mold 304. The ring 302 is slidably mounted onto the mold 304 such that the ring is capable of being translated or moved along a length of mold 304. A through hole 308 is formed through the ring 302 and is sized to allow the mold 304 to slide freely through the hole 308. Preferably, the inner diameter of the ring 302 is slightly greater than the outer diameter of the mold 304. In FIGS. 3-6, the inner surface of the ring 302 defined by the hole 308 through the ring 302 contacts the outer surface of the mold 304 during heating of the ring and mold.

Referring to FIG. 3, the blow molding apparatus 300 also includes a nozzle 310 for delivering heated air or other gas onto the ring 302. The nozzle is shown removed from the ring, as may occur after the tubular mold is initially setup with the polymer tube. The nozzle 310 is C-shaped and includes a pair of curved finger-like members 312 configured to circumferentially surround the ring. The curved finger-like members 312 include a plurality of fluid outlet ports 314 distributed along the curved inner surface 316 of the nozzle. The outlet ports 314 are in fluid communication with fluid delivery channels within the nozzle. The fluid delivery channels extend through an extension arm that connects the nozzle with a fluid source and a means for moving the ring 302 longitudinally and radially. As used herein, longitudinally refers to a direction along the central axis 320 of the tubular mold 304, as shown by an arrow 322. As used herein, radially refers to a direction perpendicular to the central axis 320 of the tubular mold 304, as exemplified by arrow 324.

Figure 4:
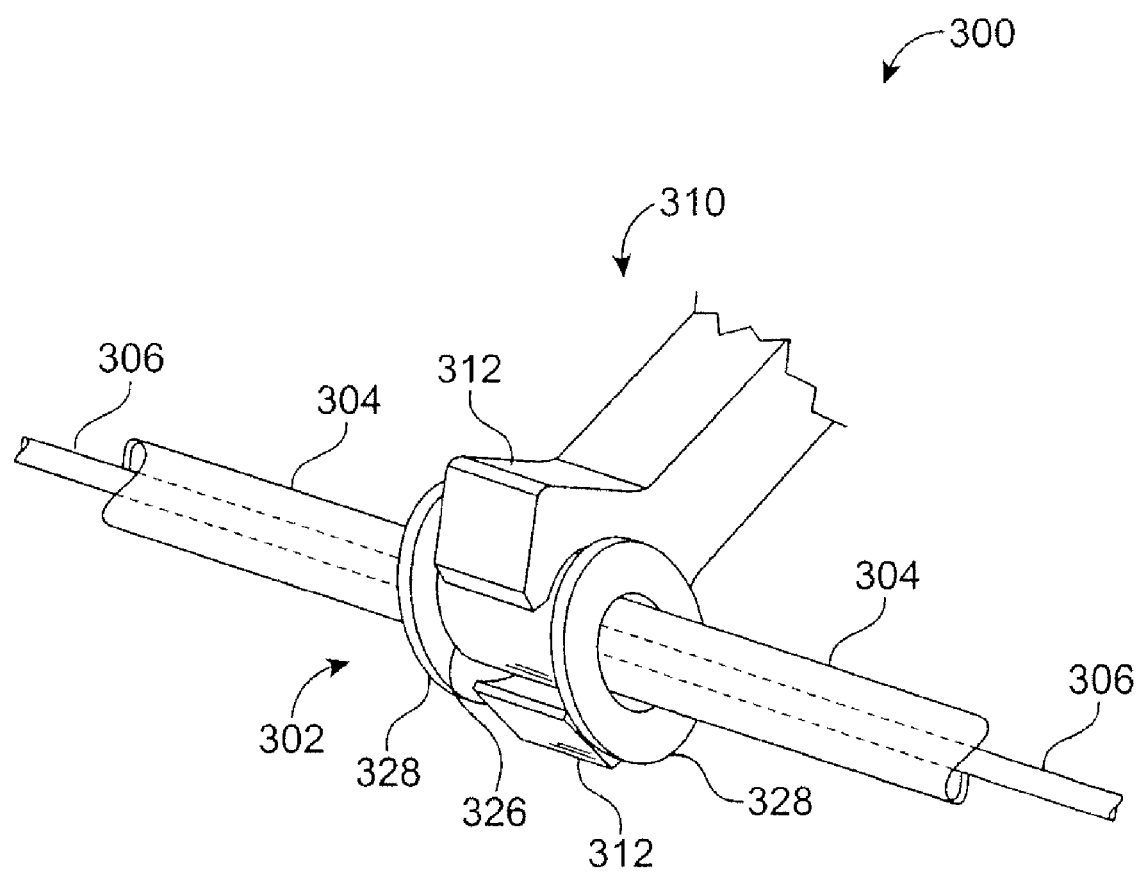
FIG. 4 is a perspective view of the blow molding apparatus of FIG. 3 showing the heating nozzle moved to a location over the ring.

FIG. 4 shows the nozzle 310 after it has been moved radially from its position in FIG. 3 to a position over the ring 302. In this position, the outlet ports 314 of the nozzle are capable of delivering heated fluid onto the ring to heat the ring. As can be seen in FIG. 4, the ring 302 and the nozzle 310 are sized and shaped to mate with each other. The ring 302 includes a cylindrical body 326 and a flange 328 at each end of the cylindrical body 328. The cylindrical body 326 has a width that is sufficient to allow the curved finger-like members 312 of the nozzle 310 to fit between the two flanges 328. Preferably, the cylindrical body 326 has an outer diameter that is smaller than the diameter of the curved inner surface 316 of the nozzle 10 shown in FIG. 3. The diameter of the curved inner surface 316 is smaller than the outer diameter of the flanges 328 so that when the nozzle 310 has been radially moved over the ring 302, subsequent longitudinal movement of the nozzle 310 will also move the ring longitudinally along the mold 304.

Figure 5:
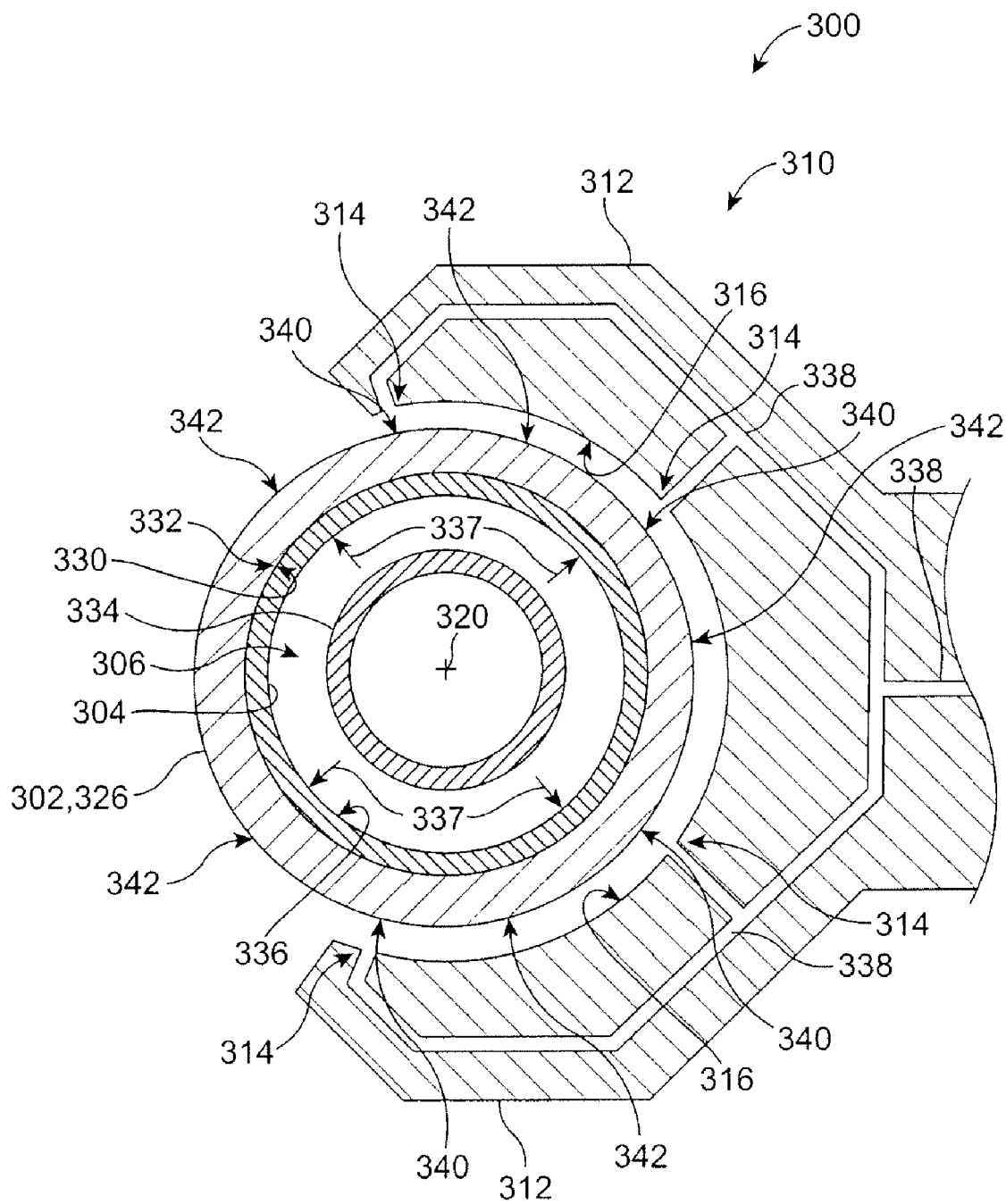
FIG. 5 is a radial cross-sectional view of the blow molding apparatus of FIG. 4 showing the unexpanded polymer tube located centrally within the mold and showing fluid channels in the ring for delivering heated fluid onto the ring.

FIG. 5 shows a radial cross-sectional view of the blow molding apparatus 300 of FIG. 4 taken through the middle of the cylindrical body 326, between the flanges 328 of ring 302. The flanges 328 are not shown for clarity and simplicity of illustration. The inner surface 330 of the ring 302 defined by the hole 308 through the ring 302 rests on the outer surface 332 of the mold 304. The unexpanded polymer tube 306 is disposed within the mold 304 such that the wall 334 of polymer tube 306 is at a distance from the inner surface 336 of the mold 304. Preferably, the polymer tube 304 is centered along the central axis 320 of the mold 304. In this way, the wall 334 of the polymer tube 304 can expand radially toward the inner surface 336 of the mold 304 in the direction of arrows 337.

Outlet ports 314 are distributed along the inner surface 316 of the nozzle and are in fluid communication with fluid channels 338 coming from a fluid source. Thus, when heated fluid is pumped through the fluid channels 338, the heated fluid exits the outlet ports 314 and is delivered directly onto the outer surfaces 340 of the cylindrical body 326 directly opposite the outlet ports 314. The ring 302 deflects heated fluid coming from the outlet ports 314 from flowing directly onto the mold 304, thereby reducing or eliminating hot spots on portions of the mold near the outlet ports 314. Because of the relatively high thermal conductivity of the ring material and because of circulation of the heated air around the ring 302, other portions 342 of the cylindrical body 326 surrounding the outer surfaces 340 directly opposite the outlet ports 314 become heated to the same or substantially same degree. The location and number of the outlet ports 314 in the nozzle 310 is carefully selected to allow for highly uniform heating of the ring 302.

Highly uniform heating of the ring 302 heats a circumference or band of the mold adjacent the ring in a highly uniform manner, which in turn, results in highly uniform heating of a circumference of the polymer tube 306 adjacent the ring. Highly uniform heating of the polymer tube 306 allows the heated circumference of the polymer tube to be radially expanded, axially deformed, or both, as desired.

Figure 6:
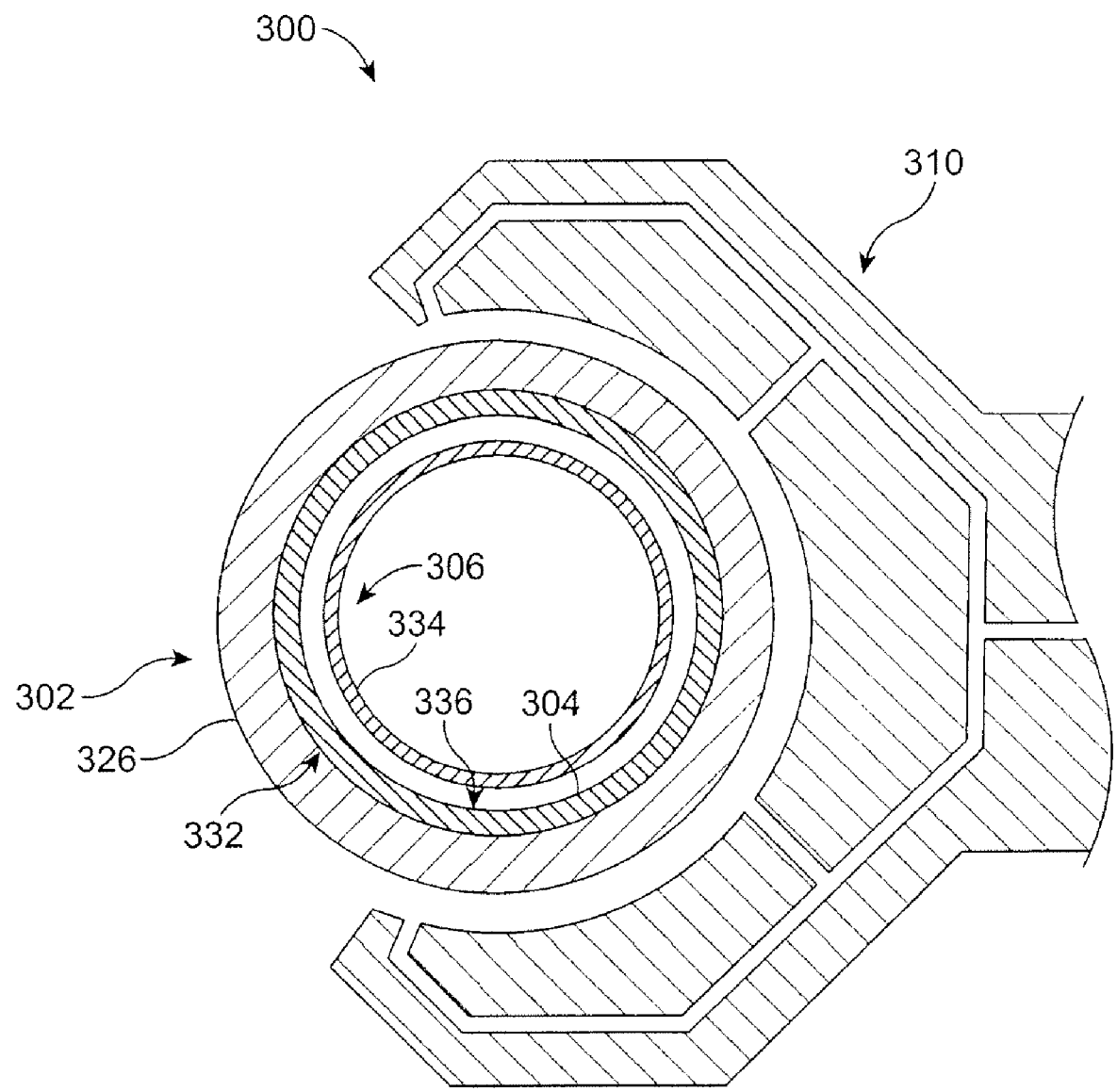
FIG. 6 is a radial cross-sectional view of the blow molding apparatus of FIG. 4 after the polymer tube has been expanded within the mold.

Referring now to FIG. 6, the heated circumference of the polymer tube 306 of FIG. 5 is shown after it has been radially expanded so that its outer diameter has increased and is almost equal to the inner diameter of the mold 304. The circumference of the expanded portion of the polymer tube 306 has also increased, which means the wall 334 of the polymer tube 306 has stretched circumferentially. Expansion of the polymer tube 306 can be achieved by conveying gas into the polymer tube 306 and increasing the pressure within polymer tube 306. This circumferential stretching or deformation orients the polymer molecules in the wall 334 in such a way that increases the hoop or circumferential strength and rigidity of the polymer tube 306. The polymer tube 306 can be radially expanded further so that its wall 334 touches the inner surface 336 of the mold 304. The diameter at the inner surface 336 of the mold 304 can be selected to correspond to the desired outer diameter of an expanded polymer tube 306.

Figure 7:
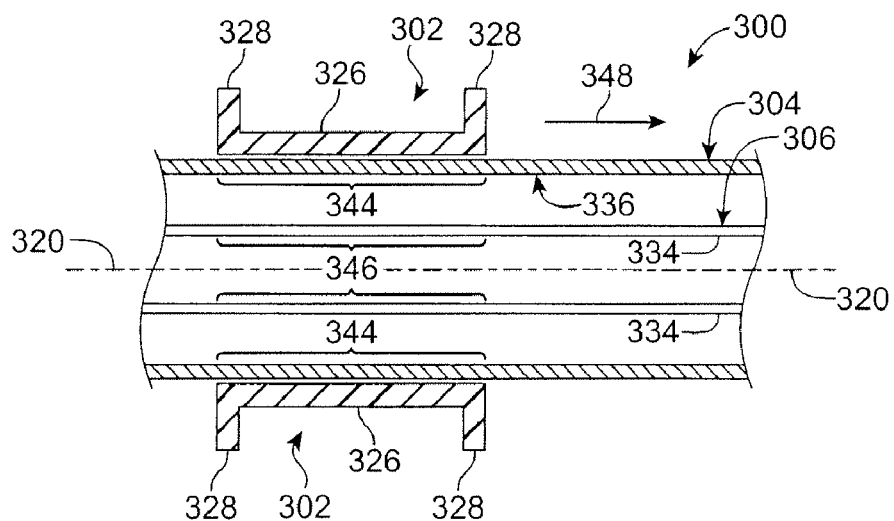
FIG. 7 is a longitudinal cross-sectional view of the blow molding apparatus of FIG. 4 showing the heated ring heating a circumference of the mold below the heated ring and showing the heated circumference of the mold heating a circumference of the polymer tube within the mold.

FIG. 7 shows a longitudinal cross-sectional view of the blow molding apparatus 300 of FIG. 4 taken along the central axis 320 of the tubular mold 304. The nozzle 310, which is normally over the ring 302 during heating, is not shown for clarity and simplicity of illustration. The heated ring 302 is shown located over the tubular mold 304. The unexpanded polymer tube 306 is disposed centrally within the mold 304. The heated ring 302 uniformly heats a circumference or band 344 of the mold 304, which, in turn, uniformly heats a circumference or band 346 of the polymer tube 306. Heating of the band 346 of the polymer tube 306 allows the polymer tube to be radially expanded by increasing pressure within the polymer tube 306. Pressure within the polymer tube 306 can be achieved by conveying gas into the polymer tube 306.

Figure 8:
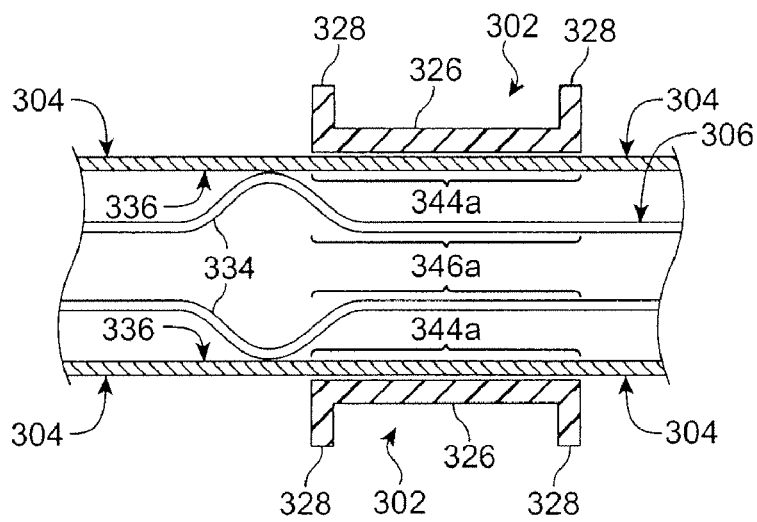
FIG. 8 is a longitudinal cross-sectional view of the blow molding apparatus of FIG. 7 after the heated ring has been translated to the right and showing a segment of the polymer tube having been radially expanded so as to touch an inner surface of the mold.

FIG. 8 shows the blow molding apparatus 300 of FIG. 7 after the uniformly heated ring 302 has been translated longitudinally to the right, as indicated by arrow 348 (FIG. 7). The polymer tube 306 can be heated to a temperature above the glass transition temperature (Tg) of the polymer of the tube 306. The heated band 346 (FIG. 7) of the polymer tube 306 has been deformed such that a portion of the polymer tube wall 334 increases in circumference and touches the inner surface 336 of the mold 304. The mold 304 limits the radial deformation of polymer tube 306 so that the outer diameter of the polymer tube does not exceed the inside diameter of the mold. Because the band 346 of polymer tube 304 has been uniformly heated, the deformed portion of the polymer tube wall 334 has a uniform thickness along its circumference. Since the heated ring 302 has been translated to the right, another band 344a of the mold 304 below the ring 302 is uniformly heated, which, in turn, uniformly heats another band 346a of the polymer tube 306 beneath the band 344a of the mold.

Figure 9:
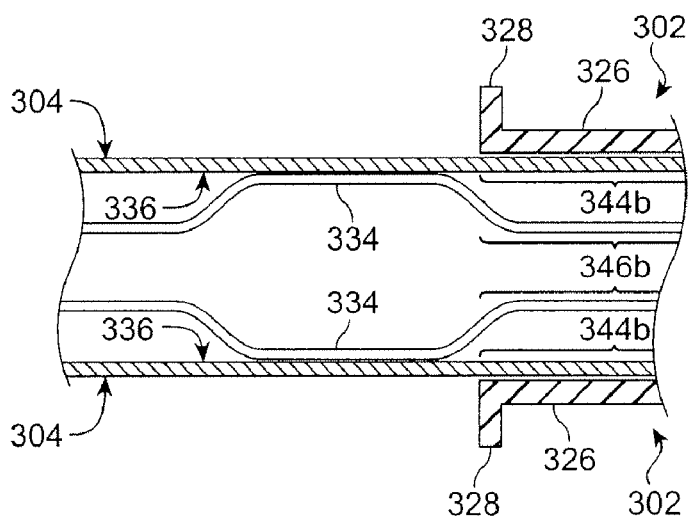
FIG. 9 is a longitudinal cross-sectional view of the blow molding apparatus of FIG. 8 after the heated ring has been translated further to the right and showing a greater segment of the polymer tube having been radially expanded and showing the mold limiting the radial expansion of the polymer tube.

FIG. 9 shows the blow molding apparatus 300 of FIG. 8 after the uniformly heated ring 302 has been translated longitudinally further to the right. The heated band 346a (FIG. 8) of the polymer tube 306 has been deformed such that a greater portion of the polymer tube wall 334 has increased in circumference and touches the inner surface 336 of the mold 304. Since the heated ring has been translated further to the right, another band 344b of the mold 304 is uniformly heated, which, in turn, uniformly heats another band 346b of the polymer tube 306 beneath the band 344b of the mold. In this manner, the polymer tube 306 is progressively deformed along its longitudinal length as the heated ring continues to be longitudinally translated.

In FIGS. 7-9, longitudinal translation of the heated ring 302 and radial expansion of the polymer tube 306 is performed continuously. That is, the heated ring 302 moves in one continuous movement from its position in FIG. 7 to its position in FIG. 9. Also, the polymer tube 306 expands continuously without interruption from its shape in FIG. 7 to its shape in FIG. 9.

In other embodiments, longitudinal translation of the heated ring 302 and radial expansion of the polymer tube 306 is performed in discrete steps. That is, the heated ring 302 stops moving after reaching its position in FIG. 8, and stops again after reaching its position in FIG. 9. In this manner, the polymer tube 306 expands in discrete steps.

Radial expansion of the polymer tube 306 in FIGS. 7-9 can be accomplished by pumping air or other gas into the polymer tube 306. The increased pressure inside the polymer tube 306 pushes the polymer tube wall 334 radially outward and places the wall 334 in circumferential tension. As a result, the heated band 346, 346a, 346b of the polymer tube 306 is deformed in a radially outward direction, thereby stretching the wall 334 at the heated band to have a greater circumference.

In other embodiments of the present invention, instead of radially expanding the polymer tube 306, the polymer tube 306 is axially deformed by longitudinally pulling one or both ends of the polymer tube 306. Pulling the ends places the polymer tube wall 334 in axial tension. As a result, the heated bands of the polymer tube 306 are deformed in an axial direction. The axial deformation orients the polymer molecules in the wall 334 in such a way that increases the axial strength and rigidity of the polymer tube 306.

In yet other embodiments, the polymer tube 306 is radially and axially deformed by longitudinally pulling the ends of the polymer tube 306 apart and increasing the air pressure inside the polymer tube 306. Pulling the ends apart while simultaneously increasing internal air pressure places the polymer tube wall 334 in axial and circumferential tension. The resulting circumferential and axial deformation orients the polymer molecules in the wall 334 in such a way that increase the circumferential and axial strength and rigidity of the polymer tube 306.

Figure 10:
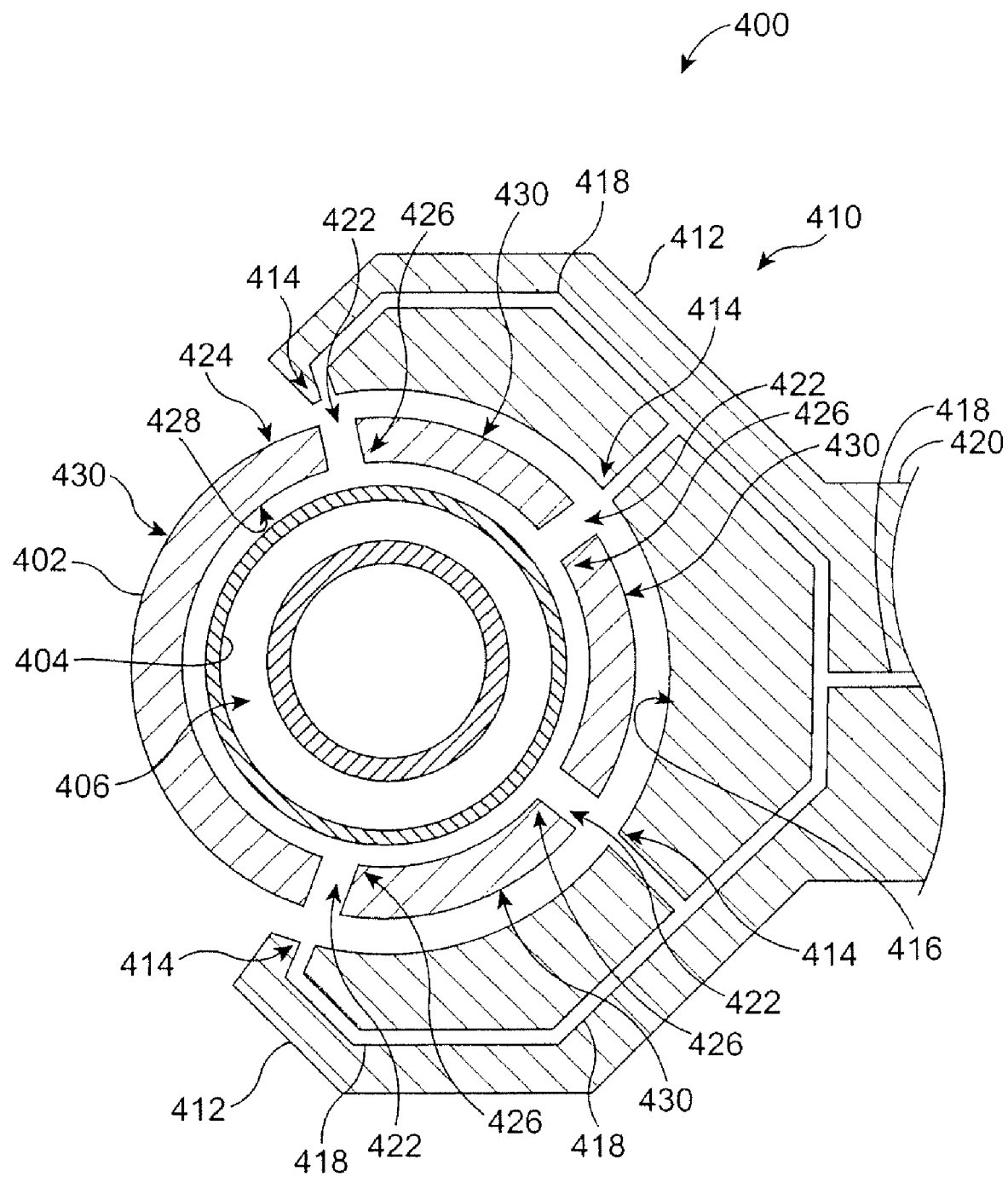
FIG. 10 is a radial cross-sectional view of a blow molding apparatus showing a nozzle disposed over a perforated ring that floats over a tubular mold when the nozzle delivers heated fluid into the perforations in the ring.

Referring next to FIG. 10, a cross-sectional view is shown of another embodiment of a blow molding apparatus 400. A ring 402 is disposed over a circumference of a tubular mold 404. An unexpanded polymer tube 406 is disposed within the mold 404. The ring 402 is slidably mounted over the mold 404 so that the ring is capable of being translated or moved along a length of mold 404. A through hole is formed through the ring 402 and is sized to allow the mold 404 to slide freely within the through hole. The inner diameter of the ring 402 is greater than the outer diameter of the mold 404.

The blow molding apparatus 400 also includes a nozzle 410 for delivering heated air or other gas onto the ring 402. The nozzle is positioned over the ring 402. The nozzle 410 is C-shaped and includes a pair of curved finger-like members 412 configured to circumferentially surround the ring. The curved finger-like members 412 include a plurality of fluid outlet ports 414 distributed along the curved inner surface 416 of the nozzle 410. The outlet ports 414 are in fluid communication with fluid delivery channels 418 within the nozzle 410. The fluid delivery channels 418 extend through an extension arm 420 that connects the nozzle 410 with a fluid source and a means for moving the nozzle 410 longitudinally and radially.

With continued reference to FIG. 10, the ring 402 includes plurality of channels 422 extending from the outer surface 424 of the ring 440 to fluid ports 426 on the inner surface 428 of the ring. Preferably, the channels 422 are distributed along the outer surface 424 so that they are beneath the fluid outlet ports 414 of the nozzle 410. In this way, the channels 422 are in communication with the fluid outlet ports 414. Heated fluid pumped through the fluid delivery channels 418 of the nozzle 410 exits the fluid outlet ports 414 and enters the channels 422 in the ring 402. The heated fluid then exits the fluid ports 426 of the ring 402 and is conveyed between the ring 402 and the mold 404 such that the ring 402 floats over the mold 404, such that there is a continuous gap between the ring 402 and the mold 404. The heated fluid circulates in the gap between the ring 402 and the mold 404 and the gap between the ring 402 and the curved inner surface of the nozzle 410. The circulating heated fluid uniformly heats the ring 402.

Because of the relatively high thermal conductivity of the ring material and because of circulation of the heated fluid around the ring 402, other portions 430 of the ring 402 located away from the channels 422 of the ring become heated to the same or substantially same degree. Uniform heating of the ring 402 uniformly heats a circumference or band of a mold adjacent the ring, which in turn, uniformly heats a circumference or band of the polymer tube 406 adjacent the ring. Uniform heating of the polymer tube 406 allows the heated band of the polymer tube to be expanded radially, axially deformed, or both, as desired.

Although the illustrated embodiment includes four fluid outlet ports 414 and four corresponding channels 426, it will be appreciated that more or less than four fluid outlet ports 414 and channels 426 may be used, as appropriate, to achieve uniform heating of the ring 402.

Figure 11:
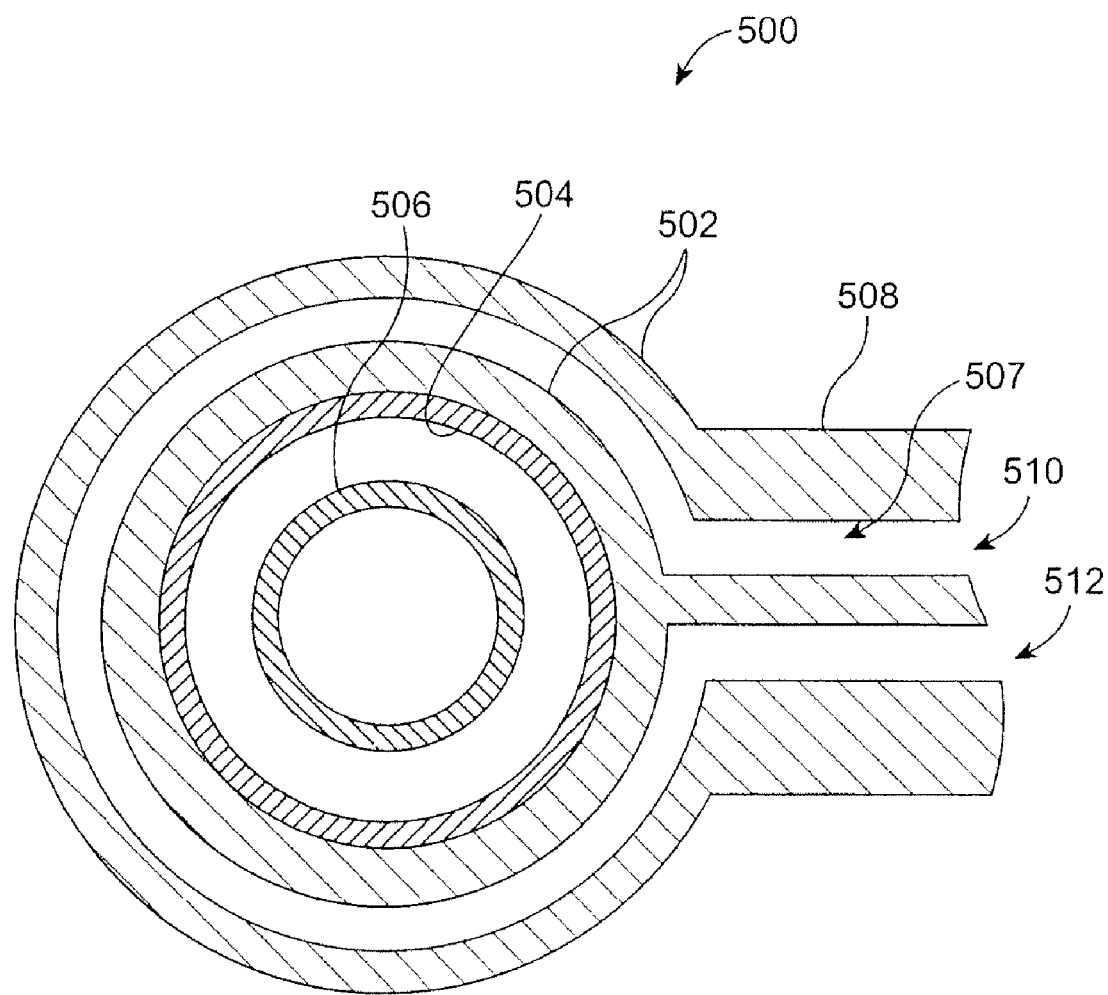
FIG. 11 is a radial cross-sectional view of a blow molding apparatus showing a fluid-carrying heating conduit within a ring for uniformly heating the ring so that a segment of a tubular mold and a segment of a polymer tube within the mold are uniformly heated.

In FIG. 11, a cross-sectional view is shown of a further embodiment of a blow molding apparatus 500. A ring 502 is disposed over a circumference of a tubular mold 504. An unexpanded polymer tube 506 is disposed within the mold 504. The ring 502 is slidably mounted over the mold 504 so that the ring is capable of being translated or moved along a length of mold 504. A through hole is formed through the ring 502 and is sized to allow the mold 504 to slide freely within the through hole. Preferably, the inner diameter of the ring 502 is greater than the outer diameter of the mold 504.

The ring includes a fluid-carrying heating conduit 507 for circulating heated fluid within the ring 502. The heated fluid may be a gas (such as air, nitrogen, oxygen, argon, etc.) or a liquid. The heating conduit 507 uniformly heats the mold 504 when it is thermally energized by heated fluid circulating through it. The heating conduit 507 preferably extends around the tubular mold 504. The fluid conduit 507 extends from the ring 502 to an extension arm 508 that connects the ring 502 with a fluid source and a means for moving ring 502 longitudinally along a length of the mold 504. The fluid conduit includes an inlet port 510 in the extension arm 508 into which the heated fluid is pumped. The heated fluid circulates through the fluid conduit 507 to uniformly heat the ring 502 and exits from an outlet port 512 in the extension arm 508.

Although the illustrated embodiment has one fluid-carrying heating conduit 507 for circulated heated fluid within the ring 502, it will be appreciated that additional fluid-carrying heating conduits may be used, as appropriate, to achieve more uniform heating. In some embodiments, the heating conduits run in opposite directions. For example, one heating conduit can run in a clockwise direction within the ring 502 while another heating conduit can run in a counter-clockwise direction within the ring. It will also be appreciated that the heating conduit(s) in the ring 502 can complete more than one revolution around the mold 504 so that more heat is transferred from the circulating heated fluid to the ring 502. Also, in some embodiments, the ring 502 comprises metal tubing coiled around a circumference of the mold 504.

Figure 12:
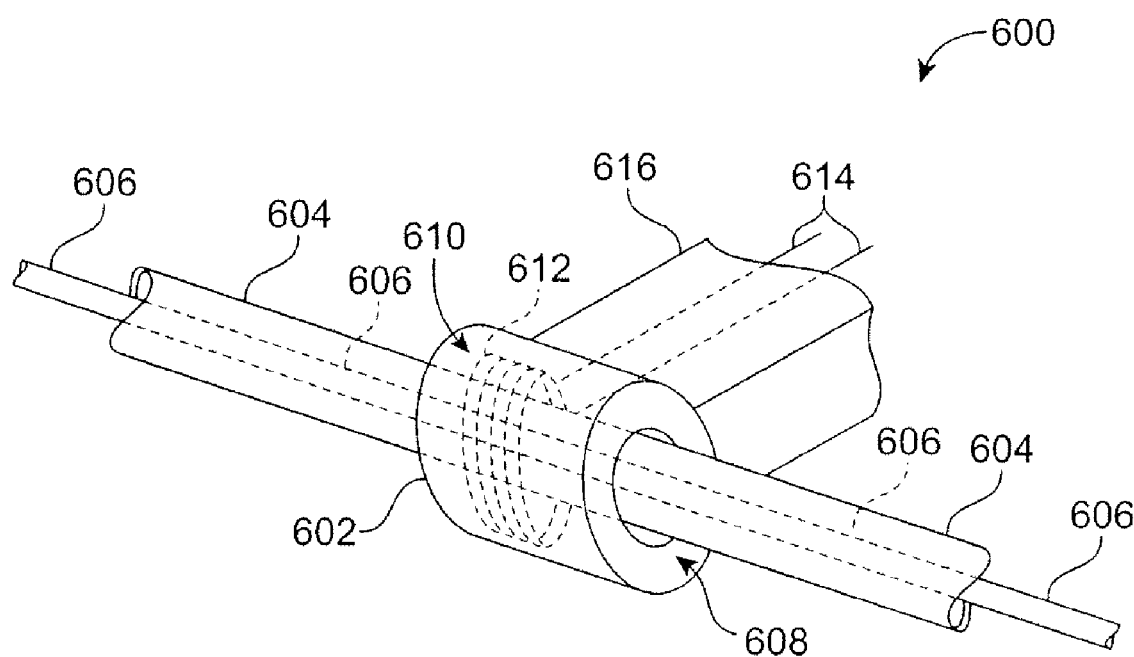
FIG. 12 is a perspective view of a blow molding apparatus showing a current-carrying heating conduit within a ring for uniformly heating the ring so that a segment of a tubular mold and a segment of a polymer tube within the mold are uniformly heated.

FIG. 12 depicts another exemplary blow molding apparatus 600 and method of the present invention. A ring 602 is disposed over a circumference of a tubular mold 604. An unexpanded polymer tube 606 is disposed within the mold 604. The ring 602 is slidably mounted on and around the mold 604 so that the ring is capable of being longitudinally translated or moved along a length of mold 604. A through hole 608 is formed through the ring 602 and is sized to allow the mold 604 to slide freely through the hole 608. Preferably, the inner diameter of the ring 602 is slightly greater than the outer diameter of the mold 604.

The ring 602 includes a current-carrying heating conduit 610 that can be thermally energized to uniformly heat the ring 602. The heating conduit 610 comprises an electrical resistive coil 612 that increases in temperature when electrical current is supplied to the coil. The coil 612 is connected to power leads 614. The power leads 614 extend through an extension arm 616 that connects the ring 602 with a means for moving ring longitudinally along a length of the mold 604. The coil 612 is distributed within the ring 602 so that the ring is uniformly heated when electrical current is supplied to the coil via the power leads 614.

In the illustrated embodiments of FIGS. 3-12, the rings 302, 402, 502, 602 extend uninterrupted as one piece around a circumference of the molds 304, 404, 504, 604, respectively. In other embodiments the ring can comprise a plurality of pieces. For example, the ring can comprise separate clamping members that move toward each other to surround a circumference of the mold. The clamping members of the ring can move toward each other until there is only a small gap between the clamping members, such that the ring does not extend completely around the mold. Alternatively, the clamping members can move toward each other until they touch, such that the ring extends completely around the mold.

After the polymer tube 306, 406, 506, 606 has been deformed to have a desired size and shape, the polymer tube is allowed to cool. Cooling the deformed polymer tube helps insure that it maintains the proper shape, size, and length following its formation. Upon cooling, the deformed polymer tube retains the length and shape imposed by an inner surface of the mold. The deformed polymer tube can be cooled slowly or quickly, such as by quenching. The deformed polymer tube can be quenched by delivering cooling fluid onto ring, the mold, and/or through the polymer tube itself. Cooling fluid can be delivered by the nozzle, by a fluid-carrying heating conduit within the ring, or by other means. The relatively high thermal conductivity of the ring facilitates uniform cooling of the deformed polymer tube.

In some embodiments, the polymer tube may be heat set after deformation from the blow molding process to relieve internal stresses within the polymer following deformation. "Heat setting" refers to allowing the polymer construct to equilibrate at a particular configuration at an elevated temperature. The pressure inside the tube, the tension along the cylindrical axis of the tube, and the temperature of the tube may be maintained above ambient levels for a period of time to allow the polymer tube to be heat set. Movement of the ring back and forth over the deformed portions of the polymer tube can facilitate heat setting and, thereby, more uniform mechanical properties through the polymer tube.

After heat setting, cooling, or both, the deformed polymer tube, now having the desired size, shape, rigidity, and strength, can be removed from the mold and further processed to form a stent or other medical device. Portions of the deformed polymer tube can be cut away to form struts, scaffolds, and/or cylindrical rings that can later be crimped down to a size appropriate for delivery into a bodily lumen.

A medicated stent may be fabricated by coating the surface of either a metallic or polymeric scaffolding with a polymeric carrier that includes an active or bioactive agent or drug. Polymeric scaffolding may also serve as a carrier of an active agent or drug.

The polymer tube that is expanded by blow molding can include a biostable biodegradable polymer, or a combination thereof. Polymers can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and eventual absorption and elimination of the polymer can be caused by, for example, hydrolysis, metabolic processes, bulk or surface erosion, and the like.

Representative examples of polymers that may be used to fabricate stents and coatings for stents of the present invention include, but are not limited to, poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen, and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating embodiments of implantable medical devices disclosed herein include ethylene vinyl alcohol copolymer (commonly known by the generic name EVOH or by the trade name EVAL), poly(butyl methacrylate), poly(vinylidene fluoride-co-hexafluoropropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, poly(vinyl acetate), styrene-isobutylene-styrene triblock copolymers, and polyethylene glycol.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. A method of manufacturing a stent, the method comprising:
   translating a heated ring disposed over a tubular mold with a polymer tube disposed within the tubular mold, wherein the heated ring heats a circumference of the mold and the polymer tube as the heated ring translates along a length of the tubular mold; and
   allowing the polymer tube to radially expand after the polymer tube is heated, wherein a nozzle positioned adjacent the ring expels a heated fluid toward the ring to heat the ring, and the nozzle includes a member with a fluid outlet port.

2. The method of claim 1, further comprising fabricating a stent from the expanded polymer tube.

3. The method of claim 1, wherein the heated ring is composed of a material having a higher thermal conductivity than the tubular mold.

4. The method of claim 1, wherein the heated ring heats the mold in a manner that reduces or prevents formation of localized hot spots on the tubular mold.

5. The method of claim 1, wherein an outward radial force on the polymer tube radially expands the heated polymer tube.

6. The method of claim 1, further comprising axially deforming the polymer tube as the heated ring translates along the tubular mold.

7. The method of claim 6, wherein an axial force on the polymer tube axially deforms the heated polymer tube.

8. The method of claim 1, wherein movement of the nozzle translates the heated ring along the length of the tubular mold.

9. The method of claim 1, wherein the heated ring includes a flange that engages the nozzle to allow the nozzle to translate the heated ring along the length of the tubular mold.

10. The method of claim 1, wherein the ring comprises a resistive heating element that heats the ring.

11. The method of claim 1, wherein the ring comprises a fluid channel; and wherein the ring is heated by a heated fluid conveyed through the fluid channel.

12. The method of claim 1, wherein the ring is made of aluminum having an anodized surface.

13. The method of claim 1, further comprising heat setting the expanded polymer tube by translating the heated ring backwards over the expanded polymer tube.

14. The method of claim 1, wherein the heated ring is a closed ring.

15. The method of claim 1, wherein the nozzle is detached from or movable relative to the ring.

16. The method of claim 1, wherein allowing the polymer tube to radially expand includes allowing the polymer tube to radially expand at a segment of the polymer tube that coincides with the location of the heated ring over tubular mold.

17. A method of manufacturing a stent, the method comprising:
   translating a heated ring disposed over a tubular mold with a polymer tube disposed within the tubular mold, wherein the heated ring heats the mold and the polymer tube; and
   allowing the polymer tube to radially expand after the polymer tube is heated,
   wherein the ring comprises a fluid port in communication with an outer surface of the tubular mold, a heated fluid is conveyed through the fluid port and between the mold and the ring, and the heated fluid is conveyed such that the ring floats over the tubular mold as a result of the heated fluid.

18. The method of claim 17, further comprising directing the heated fluid from a nozzle toward the ring, the nozzle detached from or movable relative to the ring.

19. A method of manufacturing a stent, the method comprising:
   translating a heated ring disposed over a tubular mold with a polymer tube disposed within the tubular mold, wherein the heated ring is heated by a heated fluid to allow the ring to uniformly or substantially uniformly heat around a circumference of the mold and the polymer tube as the heated ring translates along the length of the tubular mold;

conveying the heated fluid from a nozzle, the nozzle disposed over the tubular mold such that movement of the nozzle translates the heated ring; and allowing the polymer tube to radially expand as the heated ring translates along the tubular mold.

20. The method of claim 19, further comprising preventing the heated fluid from flowing directly from a nozzle outlet to the tubular mold by deflecting the heated fluid coming from the nozzle outlet.

21. The method of claim 19, further comprising conveying the heated fluid between the mold and the ring such that the ring floats over the tubular mold as a result of the heated fluid.

22. The method of claim 19, wherein the ring is disposed between the tubular mold and the nozzle.

23. The method of claim 19, wherein translating the ring includes pushing the ring with the nozzle.

24. A method of manufacturing a stent, the method comprising:

translating a heated ring disposed over a tubular mold with a polymer tube disposed within the tubular mold, wherein the heated ring includes a heating conduit disposed within the heated ring to allow the heated ring to heat around a circumference of the mold and the polymer tube as the heated ring translates along the length of the tubular mold;

thermally energizing the heating conduit while translating the heated ring; and allowing the polymer tube to radially expand after the polymer tube is heated, wherein the ring completely encircles the circumference of the tubular mold.

25. The method of claim 24, further comprising fabricating a stent from the expanded polymer tube.

26. The method of claim 24, wherein the heating conduit comprises an electrical resistive coil that heats the heated ring.

27. The method of claim 24, wherein the heating conduit is a fluid channel, the fluid channel comprising a heated fluid circulating therein to heat the ring.

28. The method of claim 24, wherein allowing the polymer tube to radially expand includes allowing the polymer tube to radially expand at a segment of the polymer tube that coincides with the location of the heated ring.

* * * * *